(12) United States Patent
Srinivasan et al.

(10) Patent No.: US 9,592,197 B2
(45) Date of Patent: *Mar. 14, 2017

(54) DOSAGE FORM CONTAINING DIPHENHYDRAMINE AND ANOTHER DRUG

(75) Inventors: Viswanathan Srinivasan, The Woodlands, TX (US); Juan Carlos Menendez, Bedford, TX (US); Venkatesh Balasubramanian, Arlington, TX (US); Somphet Peter Suphasawud, Fort Worth, TX (US); Ralph Brown, Southlake, TX (US); David Brown, Colleyville, TX (US)

(73) Assignee: SOVEREIGN PHARMACEUTICALS, LLC, Fort Worth, TX (US)

( * ) Notice: Subject to any disclaimer, the term of this patent is extended or adjusted under 35 U.S.C. 154(b) by 2274 days.

This patent is subject to a terminal disclaimer.

(21) Appl. No.: 11/012,267

(22) Filed: Dec. 16, 2004

(65) Prior Publication Data

US 2006/0134207 A1 Jun. 22, 2006

(51) Int. Cl.
- A61K 9/20 (2006.01)
- A61K 9/10 (2006.01)
- A61K 9/24 (2006.01)
- A61K 31/485 (2006.01)
- A61K 45/06 (2006.01)

(52) U.S. Cl.
CPC ............... *A61K 9/10* (2013.01); *A61K 9/209* (2013.01); *A61K 31/485* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,401,665 A | 8/1983 | Sheinaus et al. | |
| 4,755,532 A | 7/1988 | Sunshine et al. | |
| 4,786,503 A | 11/1988 | Edgren et al. | |
| 4,986,987 A | 1/1991 | Ayer et al. | |
| 5,032,401 A | 7/1991 | Jamas et al. | |
| 5,073,380 A | 12/1991 | Babu et al. | |
| 5,141,752 A | 8/1992 | Ayer et al. | |
| 5,407,686 A | 4/1995 | Patel et al. | |
| 5,445,829 A | 8/1995 | Paradissis et al. | |
| 5,681,577 A * | 10/1997 | Lech et al. | 424/439 |
| 5,807,579 A | 9/1998 | Vilkov et al. | |
| 6,126,969 A | 10/2000 | Shah et al. | |
| 6,312,728 B1 | 11/2001 | Beimann et al. | |
| 6,372,252 B1 * | 4/2002 | Blume et al. | 424/464 |
| 6,699,502 B1 | 3/2004 | Fanara et al. | |
| 6,730,321 B2 | 5/2004 | Ting et al. | |
| 6,797,283 B1 | 9/2004 | Edgren et al. | |
| 6,827,946 B2 | 12/2004 | Hirsh | |
| 6,863,901 B2 | 3/2005 | Hirsh et al. | |
| 2003/0180362 A1 | 9/2003 | Park et al. | |
| 2004/0086563 A1 | 5/2004 | Fanara et al. | |
| 2004/0220153 A1 | 11/2004 | Jost-Price et al. | |
| 2004/0229849 A1 | 11/2004 | Jost-Price et al. | |
| 2004/0253311 A1 | 12/2004 | Berlin et al. | |
| 2004/0259809 A1 | 12/2004 | Gonzales | |
| 2005/0112199 A1 | 5/2005 | Padval et al. | |
| 2005/0152967 A1 | 7/2005 | Tengler et al. | |
| 2005/0153947 A1 | 7/2005 | Padval et al. | |
| 2005/0266032 A1* | 12/2005 | Srinivasan et al. | 424/400 |
| 2006/0057205 A1* | 3/2006 | Srinivasan et al. | 424/472 |

OTHER PUBLICATIONS

U.S. Appl. No. 10/736,902 entitled "Dosage Form Containing Promethazine and Another Drug", filed Dec. 17, 2003.
U.S. Appl. No. 10/798,884 entitled "Dosage Form Containing a Morphine Derivative and Another Drug", filed Mar. 12, 2004.
U.S. Appl. No. 10/910,806 entitled "Dosage Form Containing Carbetapentane and Another Drug", filed Aug. 4, 2004.
U.S. Appl. No. 10/939,351 entitled "Phenylepherine Containing Dosage Form", filed Sep. 14, 2004.

* cited by examiner

*Primary Examiner* — Lakshmi Channavajjala
(74) *Attorney, Agent, or Firm* — Abel Law Group, LLP

(57) ABSTRACT

A pharmaceutical dosage form which comprises diphenhydramine and/or a pharmaceutically acceptable salt thereof and at least one second drug. The dosage form provides a plasma concentration within the therapeutic range of the at least one second drug over a period which is coextensive with a substantial part of the period over which the dosage form provides a plasma concentration within the therapeutic range of diphenhydramine or salt thereof. This Abstract is neither intended to define the invention disclosed in this specification nor intended to limit the scope of the invention in any way.

68 Claims, No Drawings

DOSAGE FORM CONTAINING DIPHENHYDRAMINE AND ANOTHER DRUG

BACKGROUND OF THE INVENTION

1. Field of the Invention

The present invention relates to a pharmaceutical dosage form which contains diphenhydramine and/or a pharmaceutically acceptable salt thereof in combination with at least one additional active ingredient. The dosage form releases diphenhydramine and the additional active ingredient at rates which provide pharmaceutically suitable plasma concentrations of both components over similar periods of time. The present invention also relates to a process for manufacturing the dosage form and to methods for alleviating conditions which can be alleviated by diphenhydramine and the at least one additional active ingredient.

2. Discussion of Background Information

Diphenhydramine is a histamine antagonist that possesses antihistaminic, antitussive, sedative, antimotion-sickness, antiemetic, and anticholinergic effects. It is used, for example, for the amelioration of allergic reactions, to reduce excessive coughing, for the treatment of motion sickness and the prevention and control of nausea and vomiting associated with certain types of anesthesia and surgery. Allergic reactions, in particular, which can be treated or ameliorated with diphenhydramine are often accompanied by conditions which cannot satisfactorily be ameliorated or treated with diphenhydramine, but may be treated or ameliorated by other drugs, e.g., expectorants, mucus thinning drugs, decongestants, (morphine derived) antitussives, and/or analgesics. A single dose of diphenydramine can provide a therapeutically effective plasma concentration for about 4 to 6 hours, whereas a single dose of other drugs will often provide a therapeutically effective plasma concentration for a considerably shorter or longer period. For example, a single dose of an expectorant such as guaifenesin will usually provide relief for only about one hour, and decongestants, and analgesics usually provide relief for about 3 to 8 hours per single dose. Codeine phosphate will usually provide relief for 2.9±0.7 hours. With a corresponding combination, the diphenhydramine would provide the desired therapeutic effect when the other drug has ceased to be effective or would cease to be effective while the other drug retained its therapeutic effects.

It would be desirable if patients suffering from, e.g., respiratory congestion, inflammation of the respiratory mucosa and sinus cavities, weeping eyes, rhinorrhea, eustachian tube congestion, cough, nausea, aching joints, headache and fever and related symptoms, for which diphenhydramine is indicated, would also obtain relief, over a similar time period, from one or more conditions for which drugs different from diphenhydramine are indicated, by the administration of a single dose of a dosage form such as, e.g., a tablet, liquid, syrup, suspension, capsule or gel and the like which provides both diphenhydramine and one or more other drugs. It would also be desirable to have available a dosage form which provides, in a single dose, diphenhydramine (together with or without any additional drug) over different time periods and/or at different rates, for example, in order to make diphenhydramine available as fast as possible and to also provide diphenhydramine over an extended period of time so as to maintain a therapeutic plasma concentration of diphenhydramine for as long as desired and/or possible.

SUMMARY OF THE INVENTION

The present invention provides a pharmaceutical dosage form which comprises a first drug which is selected from diphenhydramine and pharmaceutically acceptable salts thereof, and at least one second drug. The dosage form provides a plasma concentration within the therapeutic range of the at least one second drug over a period which is coextensive with at least about 60% of the period over which the dosage form provides a plasma concentration within the therapeutic range of the first drug.

In one aspect of the dosage form, the at least one second drug is preferably selected from decongestants, antitussives, expectorants, mucus thinning drugs and analgesics. For example, the at least one second drug may comprise one or more antitussives such as, e.g., codeine, dihydrocodeine, hydrocodone, dextromethorphan, carbetapentane and pharmaceutically acceptable salts thereof, and/or the at least one second drug may comprise one or more decongestants such as, e.g., phenylepherine, pseudoephedrine and pharmaceutically acceptable salts thereof, and/or the at least one second drug may comprise one or more analgesics such as, e.g., acetaminophen, aspirin, ibuprofen, naproxen, hydrocodone, oxycodone, morphine and hydromorphone, and/or the at least one second drug may comprise one or more expectorants such as, e.g., guaifenesin.

In another aspect of the dosage form of the present invention, the first drug may comprise diphenhydramine hydrochloride.

In yet another aspect, the plasma half-life of the at least one second drug may be shorter or longer than the plasma half-life of the first drug by at least about 1 hour, e.g., by at least about 2 hours, by at least about 3 hours, by at least about 4 hours, or by at least about 6 hours.

In a still further aspect, the period of a plasma concentration within the therapeutic range of the at least one second drug may be coextensive with at least about 70%, e.g., at least about 80%, at least about 90%, or at least about 95%, of the period of a plasma concentration within the therapeutic range of the first drug.

In another aspect, the dosage form may be a tablet. For example, the tablet may be a bi-layered tablet.

In another aspect, the dosage form may comprise a matrix which comprises the first drug and has dispersed therein particles which comprise the at least one second drug. For example, the matrix may provide an immediate release of the first drug and the particles may provide a controlled release of the at least one second drug. Conversely, the dosage form also may comprise a matrix which comprises the at least one second drug and has dispersed therein particles which comprise the first drug. For example, the matrix may provide an immediate release of the at least one second drug and the particles may provide a controlled release of the first drug.

In another aspect, the dosage form may comprise a liquid or semi-liquid dosage form. For example, the dosage form may comprise a solution or a suspension. In another aspect, the dosage form may comprise a suspension having particles therein which provide a controlled release of the first drug and/or of the at least one second drug.

The present invention also provides a bi-layered tablet which comprises two layers. The first layer comprises diphenhydramine and/or a pharmaceutically acceptable salt thereof. The second layer comprises at least one additional drug which is selected from decongestants, antitussives, expectorants, mucus thinning drugs and analgesics. The bi-layered tablet provides a plasma concentration within the therapeutic range of the at least one additional drug over a period which is coextensive with at least about 60% of the period over which the bi-layered tablet provides a plasma concentration within the therapeutic range of the diphenhydramine or pharmaceutically acceptable salt thereof.

In one aspect of the bi-layered tablet, the second layer may comprise one or more of phenylepherine, pseudoephedrine, carbetapentane, guaifenesin, hydrocodone, dihydrocodeine, oxycodone, hydromorphone, dextromethorphan, brompheniramine, chlorpheniramine, acetaminophen, aspirin, ibuprofen, naproxen, morphine and pharmaceutically acceptable salts thereof.

In another aspect, the first layer may comprise diphenhydramine hydrochloride and the second layer may comprise two or more of phenylepherine, pseudoephedrine, carbetapentane, diphenhydramine, guaifenesin, hydrocodone, dihydrocodeine, oxycodone, hydromorphone, dextromethorphan, brompheniramine, chlorpheniramine, acetaminophen, aspirin, ibuprofen, naproxen, morphine and pharmaceutically acceptable salts thereof.

In yet another aspect, the first layer may comprise diphenhydramine or a pharmaceutically acceptable salt thereof as the only active ingredient. For example, diphenhydramine hydrochloride may be the only active ingredient in the first layer.

In a still further aspect of the bi-layered tablet of the present invention, the period of a plasma concentration within the therapeutic range of the at least one second drug may be coextensive with at least about 70%, e.g., at least about 80%, or at least about 90%, of the period of a plasma concentration within the therapeutic range of the diphenhydramine or pharmaceutically acceptable salt thereof.

In a still further aspect of the bi-layered tablet, the first layer may be an immediate release layer and/or the second layer may be a controlled release layer.

In another aspect, the first layer of the bi-layered tablet may contain from about 1 mg to about 300 mg of diphenhydramine hydrochloride or an equivalent amount of at least one other pharmaceutically acceptable salt of diphenhydramine and/or the second layer may contain from about 1 mg to about 300 mg of diphenhydramine hydrochloride or an equivalent amount of at least one other pharmaceutically acceptable salt of diphenhydramine.

In yet another aspect of the bi-layered tablet, the second layer thereof may be a controlled release layer and may contain (i) from about 1 mg to about 120 mg of phenylepherine hydrochloride or an equivalent amount of at least one other pharmaceutically acceptable salt of phenylepherine; and/or (ii) from about 1 mg to about 240 mg of pseudoephedrine hydrochloride or an equivalent amount of at least one other pharmaceutically acceptable salt of pseudoephedrine; and/or (iii) from about 1 mg to about 120 mg of carbetapentane citrate or an equivalent amount of at least one other pharmaceutically acceptable salt of carbetapentane; and/or (iv) from about 1 mg to about 120 mg of codeine phosphate or an equivalent amount of at least one other pharmaceutically acceptable salt of codeine; and/or (v) from about 1 mg to about 30 mg of dihydrocodeine bitartrate or an equivalent amount of at least one other pharmaceutically acceptable salt of dihydrocodeine; and/or (vi) from about 1 mg to about 20 mg of hydrocodone bitartrate or an equivalent amount of at least one other pharmaceutically acceptable salt of hydrocodone; and/or (vii) from about 10 mg to about 1000 mg of acetaminophen; and/or (viii) from about 10 mg to about 1500 mg of guaifenesin. The second layer may further contain from about 1 mg to about 300 mg of diphenhydramine hydrochloride or an equivalent amount of at least one other pharmaceutically acceptable salt of diphenhydramine.

The present invention also provides a multi-layered tablet which comprises at least a first layer and a second layer. The first layer comprises diphenhydramine and/or a pharmaceutically acceptable salt thereof and the second layer is a controlled release layer and comprises at least one drug which is selected from decongestants, antitussives, expectorants, mucus thinning drugs and analgesics.

In one aspect, the first layer of the multi-layered tablet may be an immediate release layer. In another aspect, the first layer may comprise diphenhydramine or a pharmaceutically acceptable salt thereof as the only active ingredient.

In a still further aspect of the multi-layered tablet of the present invention, the second layer preferably comprises one or more, e.g., at least two, of codeine, dihydrocodeine, hydrocodone, dextromethorphan, phenylepherine, pseudoephedrine, guaifenesin and pharmaceutically acceptable salts thereof.

In another aspect of the multi-layered tablet, the at least one drug in the second layer may have a plasma half-life which is shorter or longer by at least about 1 hour, e.g., by at least 2 hours, by at least 4 hours, or by at least 6 hours, than the plasma half-life of diphenhydramine.

In another aspect, the first layer may comprise diphenhydramine hydrochloride and the multi-layered tablet may provide a plasma concentration within a therapeutic range of the at least one drug in the second layer over a period which is coextensive with at least about 80% of the period over which the multi-layered tablet provides a plasma concentration within a therapeutic range of diphenhydramine.

In a still further aspect of the multi-layered tablet, the at least one drug in the second layer may comprise one or more of codeine, dihydrocodeine, hydrocodone, dextromethorphan, phenylepherine, pseudoephedrine, guaifenesin and pharmaceutically acceptable salts thereof.

In another aspect of the multi-layered tablet of the present invention, the layers may be discrete zones which are arranged adjacent to each other, or one of the first and second layers may be partially or completely surrounded by the other one of the first and second layers, or one of the first and second layers may be coated with the other one of the first and second layers.

The present invention also provides a liquid dosage form which comprises (a) diphenhydramine and/or a pharmaceutically acceptable salt thereof and (b) at least one drug which is selected from decongestants, expectorants, mucus thinning drugs, antitussives and analgesics. This liquid dosage form provides a plasma concentration within the therapeutic range of component (b) over a period which is coextensive with at least about 60% of the period over which the liquid dosage form provides a plasma concentration within the therapeutic range of component (a).

In one aspect, the liquid dosage form may comprise a suspension.

In another aspect, at least a part of component (a) and/or of component (b) may be present as a complex with a complexing agent. For example, the complexing agent may comprise an ion-exchange resin such as, e.g., (sodium) polystyrene sulfonate.

In a still further aspect, the suspension may comprise particles of a complex of at least a part of component (a) and/or of component (b) with an ion-exchange resin, which particles are provided, at least in part, with a controlled release coating. This controlled release coating may comprise an organic polymer, e.g., a polyacrylate and/or an alkylcellulose.

The present invention also provides a method of concurrently alleviating (e.g., treating) a condition which can be alleviated by administration of diphenhydramine and at least one other condition which can be alleviated by administration of a drug which is a decongestant, antitussive, expectorant, mucus thinning drug and/or analgesic. The method comprises administering any of the pharmaceutical dosage forms set forth above, including the various aspects thereof, to a subject in need thereof.

In one aspect of the method, the condition which can be alleviated by administration of diphenhydramine comprises an allergic reaction.

In another aspect, the dosage form is preferably administered not more than about 3 times per day, e.g., twice per day.

The present invention also provides a process for manufacturing any of the pharmaceutical dosage forms discussed above, including the various aspects thereof. This method comprises the preparation of a first composition which comprises diphenhydramine and/or a pharmaceutically acceptable salt thereof and the preparation of a second composition which comprises at least one second drug, and the combining of the first and the second compositions to form the dosage form.

In one aspect of the process, the first and second compositions may be combined by using a tablet press.

The present invention furthermore provides a pharmaceutical dosage form which comprises (a) a first drug which is diphenhydramine or a pharmaceutically acceptable salt thereof and has a first plasma half-life and (b) at least one second drug which is selected from decongestants, antitussives, expectorants, mucus thinning drugs and analgesics and has a second plasma half-life which differs from the first plasma half-life by at least about 1 hour, wherein the dosage form provides a plasma concentration within a therapeutic range of the at least one second drug over a period which is coextensive with at least about 70% of a period over which the dosage form provides a plasma concentration within a therapeutic range of the first drug.

In one aspect, the first half-life may be shorter or longer by at least about 2 hours, e.g., by at least 4 hours, than the half-life of the at least one second drug.

In another aspect, the period of a plasma concentration within the therapeutic range of the at least one second drug may be coextensive with at least about 80% of the period over which the dosage form provides a plasma concentration within the therapeutic range of the first drug.

In yet another aspect, the dosage form may comprise a bi-layered tablet.

In another aspect, the dosage form may be associated with instructions to administer the dosage form about three of fewer times per day, e.g., 1, 2 or 3 times per day.

The present invention also provides a pharmaceutical dosage form which comprises (a) diphenhydramine or a pharmaceutically acceptable salt thereof in a first form or layer and (b) diphenhydramine or a pharmaceutically acceptable salt thereof in a second form or layer which is different from the first form or layer. The dosage form releases the diphenhydramine (b) over a different period and/or at a different rate than the diphenhydramine (a).

In one aspect of the dosage form, the first form or layer may be an immediate release form or layer and the second form or layer may be a controlled release form or layer.

In another aspect, the dosage form may comprise a solid dosage form. By way of non-limiting example, the dosage form may be a tablet.

In yet another aspect, the dosage form may comprise a liquid dosage form. By way of non-limiting example, the dosage form may be a suspension.

In a still further aspect, the dosage form may be a multi-layered tablet which comprises at least one immediate release layer and at least one controlled release layer which independently comprise diphenhydramine and/or a pharmaceutically acceptable salt thereof and wherein at least one of the layers of the multi-layered tablet comprises an additional drug.

In yet another aspect, the dosage form may comprise at least one additional drug selected from decongestants, antitussives, expectorants, mucus thinning drugs and analgesics.

In another aspect, the dosage form may comprise a liquid which comprises diphenhydramine or a pharmaceutically acceptable salt thereof in uncomplexed form and diphenhydramine or a pharmaceutically acceptable salt thereof as a complex with a complexing agent. For example, the complexing agent may comprise an ion-exchange resin.

In another aspect, the dosage form may release diphenhydramine and/or a pharmaceutically acceptable salt thereof independently over a first period and over a second period and not more than about 30% of the second period may be coextensive with all or a part of the first period.

The pharmaceutical dosage form which constitutes one of the aspects of the present invention comprises a first drug which is selected from diphenhydramine and pharmaceutically acceptable salts thereof. The preferred salt of diphenhydramine is the hydrochloride. However, other pharmaceutically acceptable salts of diphenhydramine may be used as well. The term "pharmaceutically acceptable salt" as used herein and in the appended claims refers to those salts of a particular drug that are not substantially toxic at the dosage administered to achieve the desired effect and do not independently possess significant pharmacological activity. The salts included within the scope of this term are pharmaceutically acceptable acid addition salts of a suitable inorganic or organic acid. Non-limiting examples of suitable inorganic acids are, for example hydrochloric, hydrobromic, sulfuric and phosphoric acids. Non-limiting examples of suitable organic acids include carboxylic acids, such as acetic, propionic, tannic, glycolic, lactic, pyruvic, malonic, succinic, fumaric, malic, tartaric, citric, cyclamic, ascorbic, maleic, hydroxymaleic, benzoic, phenylacetic, 4-aminobenzoic, 4-hydroxybenzoic, anthranillic, cinnamic, salicylic, 4-aminosalicyclic, 2-phenoxybenzoic, 2-acetoxybenzoic and mandelic acids, as well as sulfonic acids, such as methanesulfonic, ethanesulfonic, and β-hydroxyethanesulfonic acids.

In addition to the diphenhydramine and/or pharmaceutically acceptable salt thereof, some dosage forms of the present invention may contain one or more (e.g., one, two or three) second drugs. Preferred, non-limiting examples of such second drugs are decongestants (such as, e.g., phenylepherine, pseudoephedrine and pharmaceutically acceptable salts thereof), antitussives (such as, e.g., codeine, dihydrocodeine, hydrocodone, dextromethorphan and pharmaceutically acceptable salts thereof), expectorants and mucus thinning drugs (such as, e.g., guaifenesin) and analgesics (such as, e.g., aspirin, acetaminophen, ibuprofen, hydrocodone, oxycodone and pharmaceutically acceptable salts thereof).

If an additional (second) drug is present, the dosage form provides a plasma concentration within the therapeutic range of the at least one second drug over a period which is coextensive with (overlaps) at least about 60%, e.g., at least about 70%, more preferred at least about 80%, e.g., at least about 90%, at least about 95%, or about 100%, of the period over which the dosage form provides a plasma concentration within the therapeutic range of the diphenhydramine. The term "therapeutic range" as used herein and in the appended claims refers to the range of drug levels (including active metabolite levels) within which most patients will experience a significant therapeutic effect (including alleviation of symptoms) without an undesirable degree of adverse reactions. It is noted that the term "coextensive with" does not exclude, but rather includes, cases where a part of the period over which the plasma concentration of the at least one second drug (and/or active metabolites thereof) is within the therapeutic range is outside the period over which the plasma concentration of the diphenhydramine is within the therapeutic range. In other words, even if the corresponding period for the at least one second drug is to overlap, for example, 70% of the corresponding period of the first drug, a certain percentage (preferably not more than about 30%, e.g., not more than about 20%, not more than about 10% or even not more than about 5%) of the total period over which the plasma concentration of the at least one second drug is within the therapeutic range may be outside the period over which the plasma concentration of the diphenhydramine and/or salt thereof is within the therapeutic range.

The period over which the therapeutic range of a particular drug may be provided in a given case depends, at least in part, on the plasma half-life of the drug and/or active metabolites thereof. The term "plasma half-life" as used herein and in the appended claims refers to the time required for the plasma drug concentration to decline by 50%. The shorter the plasma half-life of a particular drug, the shorter will be the period within the therapeutic range of the drug which is provided by a single administered dose of the drug. In one preferred aspect of the dosage form of the present invention, the plasma half-life of the at least one second drug will be shorter or longer than the plasma half-life of the diphenhydramine by at least about 1 hour, e.g., by at least about 2 hours, by at least about 3 hours, by at least about 4 hours, by at least about 6 hours, by at least about 8 hours, by at least about 10 hours, or even by at least about 12 hours.

A preferred, although non-limiting, embodiment of the dosage form of the present invention is a tablet, in particular, a bi-layered tablet. Non-limiting examples of other embodiments of the dosage form of the invention are capsules, pills, chewable tablets, suspensions, solutions, syrups, suppositories and transdermal patches.

The bi-layered tablet which forms another aspect of the present invention comprises two layers. The first layer comprises diphenhydramine and/or a pharmaceutically acceptable salt thereof, as discussed above. The second layer comprises at least one additional drug which is selected from decongestants, antitussives, expectorants, mucus thinning drugs and analgesics. Specific and non-limiting examples of such drugs are given above. The bi-layered tablet provides a plasma concentration within the therapeutic range of the at least one additional drug over a period which is coextensive with at least about 60%, or at least about 70%, preferably at least about 80%, e.g., at least about 90% or even about 100% of the period over which the bi-layered tablet provides a plasma concentration within the therapeutic range of the diphenhydramine.

In a preferred aspect of the bi-layered tablet, the diphenhydramine and/or pharmaceutically acceptable salt thereof (in particular, diphenhydramine hydrochloride) is the only active ingredient in the first layer. The second layer will usually contain one, two, three or even more additional active ingredients.

In another preferred aspect of the bi-layered tablet, the first layer is an immediate release layer and the second layer is a controlled release layer. The term "controlled release layer" as used herein and in the appended claims refers to any layer that is not an immediate release layer, i.e., does not release all of the active ingredients contained therein within a relatively short time (for example, within less than 1 hour, e.g., less than 0.5 hours, following ingestion of the dosage form). Accordingly, this term is a generic term which encompasses, e.g., sustained (extended) release layers, pulsed release layers, delayed release layers, and the like. Preferably, the controlled release layer releases the one or more active ingredients contained therein continuously or intermittently and, preferably, in approximately equal amounts per time unit, over an extended period of time such as, e.g., at least about 2 hours, at least about 3 hours, at least about 4 hours, at least about 6 hours, at least about 8 hours, at least about 10 hours, at least about 12 hours, at least about 16 hours, or at least about 24 hours. The desirable length of the time period of continuous or intermittent (e.g., pulsed) release depends, inter alia, on the plasma half-life of the drug and/or an active metabolite thereof.

The first layer of the bi-layered tablet of the present invention will usually contain at least about 10 mg, e.g., at least about 20 mg, at least about 40 mg, at least about 70 mg, or at least about 90 mg of diphenhydramine hydrochloride or an equivalent amount (in terms of molar amount) of diphenhydramine and/or any other pharmaceutically acceptable salt thereof. Usually, the first layer will not contain more than about 150 mg, e.g., not more than about 120 mg, or not more than about 100 mg of diphenhydramine hydrochloride or an equivalent amount of diphenhydramine and/or any other pharmaceutically acceptable salt thereof.

The second layer of the bi-layered tablet preferably is a controlled release layer, in particular, a sustained release layer. The controlled release layer may contain, by way of non-limiting example, (i) diphenhydramine hydrochloride, usually in an amount which is not less than about 0.1 mg, e.g., not less than about 1 mg, not less than about 2.5 mg, not less than about 20 mg, not less than about 50 mg, or not less than about 90 mg, but not more than about 150 mg, e.g., not more than about 120 mg, or not more than about 100 mg, or an equivalent amount of diphenhydramine and/or any other pharmaceutically acceptable salt thereof, alone or in combination with: (ii) phenylepherine hydrochloride, usually in an amount which is not less than about 1 mg, e.g., not less than about 10 mg, not less than about 15 mg, or not less than about 25 mg, but not more than about 125 mg, e.g., not more than about 100 mg, or an equivalent amount of phenylepherine and/or any other pharmaceutically acceptable salt thereof; and/or (iii) pseudoephedrine hydrochloride, usually in an amount which is not less than about 1 mg, e.g., not less than about 10 mg, not less than about 25 mg, or not less than about 50 mg, but not more than about 240 mg, e.g., not more than about 150 mg, not more than about 100 mg, or not more than about 70 mg, or an equivalent amount of pseudoephedrine and/or any other pharmaceutically acceptable salt thereof; and/or (iv) carbetapentane citrate, usually in an amount which is not less than about 1 mg, e.g., not less than about 5 mg, not less than about 10 mg, not less than about 25 mg, or not less than about 50 mg, but not more than about 120 mg, e.g., not more than about 100 mg, not more than about 70 mg, or not more than about 60 mg, or an equivalent amount of carbetapentane and/or any other pharmaceutically acceptable salt thereof; and/or (v) codeine phosphate, usually in an amount which is not less than about 1 mg, e.g., not less than about 10 mg, not less than about 25 mg, or not less than about 30 mg, but not more than about 120 mg, e.g., not more than about 80 mg, not more than about 60 mg, or not more than about 45 mg, or an equivalent amount of codeine and/or any other pharmaceutically acceptable salt thereof; and/or (vi) dihydrocodeine bitartrate, usually in an amount which is not less than about 1 mg, e.g., not less than about 5 mg, but not more than about 30 mg, e.g., not more than about 20 mg, or an equivalent amount of dihydrocodeine and/or any other pharmaceutically acceptable salt thereof; and/or (vii) hydrocodone bitartrate, usually in an amount which is not less than about 1 mg, e.g., not less than about 5 mg, but not more than about 20 mg, e.g., not more than about 15 mg, or an equivalent amount of hydrocodone and/or any other pharmaceutically acceptable salt thereof; and/or (viii) acetaminophen, usually in an amount which is not less than about 10 mg, e.g., not less than about 50 mg, or not less than about 100 mg, but not more than about 1000 mg, e.g., not more than about 500 mg, or not more than about 250 mg; and/or (ix) guaifenesin, usually in an amount which is not less than about 10 mg, e.g., not less than about 50 mg, or not less than about 100 mg, but not higher than about 1600 mg, e.g., not higher than about 1000 mg, or not higher than about 500 mg.

Another aspect of the present invention is a multi-layered tablet which comprises at least a first layer and a second layer, but may optionally comprise a third, fourth, fifth, etc. layer. The first layer, which preferably is an immediate release layer, comprises diphenhydramine and/or a pharmaceutically acceptable salt thereof (preferably as the only active ingredient contained therein) and the mandatory second layer is a controlled release layer and may comprise at least one drug which is selected from decongestants, antitussives, expectorants, mucus thinning drugs and analgesics. If more than one additional drug is to be incorporated in the tablet, the second layer may contain all of the additional drugs. Alternatively, a separate (third) layer may be provided for the second additional drug, for example, in cases where it would be difficult to design a controlled release layer which provides a desired release rate for both the first and the second additional drug. Of course, a fourth, fifth, etc. layer may be provided for a third or fourth additional drug, and so on. Alternatively and by way of non-limiting example, the second and a third layer may contain the same drug or drugs, but in different (relative) concentrations and/or incorporated in a different controlled release formulation. Of course, it is also possible for at least one of the third, fourth, etc. drugs to be present in the first layer.

The multi-layered tablet of the present invention will usually be made up of two or more distinct layers or discrete zones of granulation compressed together with the individual layers lying on top of one another. Layered tablets have the appearance of a sandwich because the edges of each layer or zone are exposed. Such conventional layered tablets are generally prepared by compressing a granulation onto a previously compressed granulation. The operation may be repeated to produce multi-layered tablets of more than two layers. In a preferred embodiment of the multi-layered tablet of the present invention, the tablet consists of two layers.

It is to be noted that it is not necessary for the two or more individual layers of the multi-layered tablet of the present invention to lie on top of one another. By way of non-limiting example, a second layer (e.g., sustained release layer) may be partially or completely surrounded by a first layer (e.g., an immediate release layer). For example, the second layer may be coated with the first layer. In the case of three layers, for example, the third layer may be partially or completely coated with the second layer, which in turn may be partially or completely coated with the first layer. Of course, these are but a few examples of the many different ways in which the various layers of the multi-layered tablet of the present invention can be arranged relative to each other. Moreover, it is to be understood that the tablets of the present invention are not limited to such multi-layered tablets. By way of non-limiting example, the tablet may comprise an immediate release matrix which comprises diphenhydramine and/or a pharmaceutically acceptable salt thereof, which matrix has dispersed therein particles of one or more sustained release formulations which have any of the other desired drug(s) incorporated therein, or the immediate release matrix comprises any of the other desired drug(s) and has dispersed therein particles of one or more sustained release formulations of diphenhydramine and/or a pharmaceutically acceptable salt thereof.

In another aspect of the multi-layered tablet of the present invention, at least one drug in the first or second layer (and/or in the additional layers) may have a plasma half-life which is shorter or longer by at least about 1 hour, e.g., by at least about 2 hours, by at least about 4 hours, or by at least about 6 hours, than the plasma half-life of diphenhydramine.

In another aspect of the multi-layered tablet, the tablet may provide a plasma concentration within a therapeutic range of the at least one drug in the second layer (e.g., one or more of phenylepherine, pseudoephedrine, carbetapentane, codeine, dihydrocodeine, hydrocodone, oxycodone, morphine, ibuprofen, acetaminophen and guaifenesin and pharmaceutically acceptable salts thereof such as, e.g., phenylepherine HCl, pseudoephedrine HCl, carbetapentane citrate, codeine phosphate, dihydrocodeine bitartrate, hydrocodone bitartrate, oxycodone hydrochloride and morphine sulfate) over a period which is coextensive with at least about 70%, e.g., at least about 80%, or at least about 90% of the period over which the multi-layered tablet provides a plasma concentration within the therapeutic range of the drug in the first layer, preferably diphenhydramine hydrochloride.

Another aspect of the present invention is constituted by a liquid dosage form, preferably a suspension, which comprises (a) diphenhydramine and/or a pharmaceutically acceptable salt thereof and (b) at least one drug which is selected from decongestants, expectorants, mucus thinning drugs, antitussives and analgesics. This liquid dosage form provides a plasma concentration within the therapeutic range of component (b) over a period which is coextensive with at least about 60%, e.g., at least about 70%, preferably at least 80%, e.g., at least 90%, of the period over which the liquid dosage form provides a plasma concentration within the therapeutic range of component (a). This may be accomplished in various ways. By way of non-limiting example, component (b) may be incorporated into a solid controlled release formulation. For example, particles of component (b) may be provided with a controlled release coating (e.g. a controlled release coating comprising an organic polymer such as, e.g., a polyacrylate or an alkylcellulose such as, e.g., ethylcellulose). This formulation may then be comminuted, if necessary, in an appropriate manner (e.g., by milling) to form particles of a size which is small enough to be suitable for being suspended in a pharmaceutically acceptable liquid carrier. Component (a), on the other hand, may be used as such or incorporated in a solid immediate release formulation, comminuted and incorporated into the liquid carrier as well. Of course, depending on the characteristics of component (b) compared to those of component (a) it may also be desirable to instead provide component (a) with a controlled release coating and to use component (b) as such or incorporated in a solid immediate release formulation.

Further, prior to incorporating components (a) and (b) into a pharmaceutically acceptable liquid carrier to form a liquid dosage form according to the present invention, at least a part of component (a) and/or at least a part of component (b) may be transformed into a complex with a complexing agent. Non-limiting examples of suitable complexing agents comprise ion-exchange resins such as, e.g., (sodium) polystyrene sulfonate.

The dosage forms of the present invention can be manufactured by processes which are well known to those of skill in the art. For example, for the manufacture of bi-layered tablets, the active ingredients may be dispersed uniformly into a mixture of excipients, for example, by high shear granulation, low shear granulation, fluid bed granulation, or by blending for direct compression. Excipients may include diluents, binders, disintegrants, dispersants, lubricants, glidants, stabilizers, surfactants and colorants. Diluents, also termed "fillers", are typically used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Binders impart cohesive qualities to a tablet formulation and are used to ensure that a tablet remains intact after compression. Non-limiting examples of suitable binders include starch (including corn starch and pregelatinized starch), gelatin, sugars (e.g., glucose, dextrose, sucrose, lactose, mannitol and sorbitol), celluloses, polyethylene glycol, waxes, natural and synthetic gums, e.g., guar gum, acacia, tragacanth, sodium alginate, and synthetic polymers such as polymethacrylates and polyvinylpyrrolidone. Lubricants facilitate tablet manufacture; non-limiting examples thereof include magnesium stearate, calcium stearate, stearic acid and polyethylene glycol. Disintegrants facilitate tablet disintegration after administration, and non-limiting examples thereof include starches, alginic acid, cross-linked polymers such as, e.g., cross-linked polyvinylpyrrolidone, croscarmellose sodium, potassium or sodium starch glycolate, clays, celluloses, starches, gums and the like. Non-limiting examples of suitable glidants include silicon dioxide, talc and the like. Stabilizers inhibit or retard drug decomposition reactions, including oxidative reactions. Surfactants may be anionic, cationic, amphoteric or nonionic. If desired, the tablets may also contain minor amounts of nontoxic auxiliary substances such as pH buffering agents, preservatives, e.g., antioxidants, wetting or emulsifying agents, solubilizing agents, coating agents, flavoring agents, and the like.

Extended/sustained release formulations may be made by choosing the right combination of excipients that slow the release of the active ingredients by coating or temporarily bonding or decreasing the solubility of the active ingredients. Examples of these excipients include cellulose ethers such as hydroxypropylmethylcellulose (e.g., Methocel K4M), polyvinylacetate-based excipients such as, e.g., Kollidon SR, and polymers and copolymers based on methacrylates and methacrylic acid such as, e.g., Eudragit NE 30D.

There are several commercially available tablet presses capable of making bi-layered tablets. For example, Manesty RotaPress Diamond, a 45 station D tooling press, is capable of making bi-layered tablets described in this application. Non-limiting examples of presses for the manufacture of bi-layered tablets include Fette America Model No. PT 3090; Maneklal Global Exports (Mumbai, India) Models JD and DH series; Niro Pharma Systems, Model R292F; and Korsch AG Models XL 800 and XL 400.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show the present invention in more detail than is necessary for the fundamental understanding of the present invention, the description making apparent to those skilled in the art how the several forms of the present invention may be embodied in practice.

Example 1

Liquid Formula

A liquid dosage form in accordance with the present invention which comprises diphenhydramine hydrochloride, dihydrocodeine bitartrate and phenylepherine hydrochloride is illustrated as follows:

| Ingredients | Per 5 mL | Per 425 L |
| --- | --- | --- |
| Diphenhydramine Hydrochloride USP | 12.5 mg | 1.063 kg |
| Dihydrocodeine Bitartrate USP | 10.0 mg | 0.850 kg |
| Phenylepherine Hydrochloride USP | 10.0 mg | 0.850 kg |
| Methyl Paraben USP | 9.0 mg | 0.765 kg |
| Propyl Paraben USP | 1.0 mg | 0.085 kg |
| Propylene Glycol USP | 259 mg | 22.016 kg |
| Saccharin Sodium USP | 3.18 mg | 0.270 kg |
| Citric Acid USP | 5.0 mg | 0.425 kg |
| Strawberry Flavor | 10 mg | 0.850 kg |
| Banana Flavor | 10 mg | 0.850 kg |
| Sorbitol Solution 70% USP | 3212.5 mg | 273.1 kg |
| Purified Water, as required to q.s. to | 5.0 mL | 425 L |

Manufacturing process for 425 L batch size: In a suitably sized stainless steel vessel, dissolve methyl paraben and propyl paraben in approximately 50 L of warm (about 45° C.), purified water. Add about half of the propylene glycol and mix for about 1 hr. In a separate 1000 L stainless steel tank equipped with a suitably sized agitator, add about 50 L of purified water. With the agitator on, add phenylepherine hydrochloride, diphenhydramine hydrochloride, saccharin sodium and citric acid and dissolve. Add the previously prepared paraben/propylene glycol solution to the 1000 L tank. Rinse the first vessel with about 2 L of water and transfer the rinsate to the 1000 L tank. Add the remaining propylene glycol to a suitably sized stainless steel vessel and dissolve the strawberry and banana flavors. Transfer this to the 1000 L tank. Rinse the container with 2 L of purified water and transfer to the 1000 L tank. With the agitator on, add the sorbitol solution 70% to the 1000 L tank. In a suitably sized stainless steel vessel, dissolve the dihydrocodeine bitartrate in about 5 L of purified water and transfer to the 1000 L tank. Rinse the container with about 2 L of purified water and transfer to the 1000 L tank. Stop the agitator and let the solution stand for 15 minutes. Adjust pH to 3.5 to 5.5 with either HCl or NaOH, qs to 425 L with purified water. Filter product through a 1 micron filter and fill in appropriately sized containers.

To make products with other analgesics, decongestants, antitussives or expectorants, one or more combinations of each of the ingredients in a range as described in Table 1 below can be made depending on the specific therapeutic effect desired.

Example 2

Suspension Formula

A suspension formula in accordance with the present invention which comprises diphenhydramine hydrochloride and phenylepherine tannate is illustrated as follows:

| Ingredients | 100 mL | 833.33 L |
| --- | --- | --- |
| Diphenhydramine Hydrochloride | 0.250 | 2.083 |
| Phenylepherine Tannate | 0.800 | 6.667 |
| Silica, colloidal anhydrous, NF | 1.73 | 14.417 |
| Hydroxyethylcellulose, NF | 0.05 | 0.417 |
| Sorbitol Solution 70% (non-crystallizing), NF | 34.00 | 283.333 |
| Glycerol | 15.00 | 125.000 |
| Xylitol, NF | 16.00 | 133.333 |
| Sodium Citrate, USP | 2.00 | 16.667 |
| Saccharin Sodium cryst., USP, | 0.01 | 0.083 |
| Sodium Benzoate, NF | 0.15 | 1.250 |
| Citric Acid Monohydrate, USP | 0.16 | 1.333 |
| Strawberry Flavor | 0.15 | 1.250 |
| Banana Flavor | 0.15 | 1.250 |
| Purified Water | QS | QS |
| Total Amount | 100 mL | 833.33 L |

Manufacturing process for 833.33 L batch: In a suitably sized stainless steel vessel, dissolve saccharin sodium, sodium benzoate, citric acid, and sodium citrate in approximately 50 L of warm (about 45° C.), purified water. In another large stainless steel drum mix the silica, diphenhydramine hydrochloride and micronized phenylepherine tannate until a uniform and consistent mixture is obtained. In a separate 1000 L stainless steel tank equipped with a suitably sized homogenizer/disperser add about 100 L of purified water. With the homogenizer on, add the silica mixture containing phenylepherine tannate and diphenhydramine hydrochloride. Add the previously prepared solution of saccharin sodium, sodium benzoate, citric acid, and sodium citrate to the 1000 L tank. Rinse the first vessel with about 2 L of water and transfer the rinsate to the 1000 L tank. Add the remaining ingredients, qs to 833.33 L and homogenize for 15 minutes. Filter product through a 10 micron filter and fill in appropriately sized containers.

To make products with other antihistamines, decongestants, antitussives, or expectorants, one or more combinations of each of the ingredients in a range as described in Table 1 below can be made depending on the specific therapeutic effect desired.

Example 3

Bi-Layered Tablet (Direct Compression)

A bi-layered tablet in accordance with the present invention which comprises diphenhydramine hydrochloride in one layer and phenylepherine hydrochloride and diphenhydramine hydrochloride in the other layer is illustrated as follows:

| Ingredients | Weight/tablet (mg) | Weight/1 kg batch (in grams) |
| --- | --- | --- |
| Layer 1 (Immediate release) | | |
| Diphenhydramine Hydrochloride | 100.00 | 137.9 |
| Silicified Microcrystalline Cellulose | 114.0 | 157.2 |
| Sodium Starch Glycolate | 10.0 | 13.8 |
| Magnesium Stearate | 1.0 | 1.38 |
| Layer 2 (Sustained release) | | |
| Phenylepherine HCl | 20.0 | 27.6 |
| Diphenhydramine Hydrochloride | 100.0 | 137.9 |
| Lactose Monohydrate | 50.0 | 68.97 |
| Dicalcium Phosphate | 50.0 | 68.97 |
| Kollidon SR | 260.0 | 358.6 |
| Stearic acid | 15.0 | 20.7 |
| Magnesium Stearate | 5.0 | 6.9 |
| Total | 725.00 | 1000.0 |

Manufacturing Process (a) Immediate release layer: Screen all ingredients through a USP sieve size #30. Blend diphenhydramine hydrochloride, silicified microcrystalline cellulose and sodium starch glycolate in a twin shell blender for 20 minutes. Add magnesium stearate which acts as a lubricant, to the above blend and mix for 3 minutes.

(b) Sustained release layer: Screen all ingredients through a USP sieve size #30. Preblend a portion (about ⅓) of the Kollidon SR and all the diphenhydramine hydrochloride for 15 minutes. Add the remaining Kollidon SR, phenylepherine hydrochloride, lactose monohydrate and dicalcium phosphate to the above preblend and mix for an additional 20 minutes. Add stearic acid and magnesium stearate to the above blend and mix for three minutes.

Manufacture bi-layered tablets using a rotary bi-layer tablet press where in each tablet the immediate release layer is 225 mg and the sustained release layer is 500 mg.

By using the process described above, a bi-layered tablet of the following composition may be manufactured through direct compression:

| Ingredients | Weight/tablet (mgs) |
| --- | --- |
| Layer 1 (Immediate Release) | |
| Diphenhydramine Hydrochloride | 50 |
| Silicified Microcrystalline Cellulose | 133.5 |
| Sodium Starch Glycholate | 15 |
| Magnesium Stearate | 1.5 |
| Layer 2 (Sustained Release) | |
| Phenylepherine HCl | 20 |
| Diphenhydramine Hydrochloride | 50 |
| Dicalcium Phosphate | 100 |
| Kollidon SR | 260 |
| Stearic Acid | 15 |
| Magnesium Stearate | 5 |
| Total | 650 |

Example 4

Bi-Layered Tablet (Wet Granulation)

A bi-layered tablet in accordance with the present invention which comprises diphenhydramine hydrochloride in one layer and pseudoephedrine hydrochloride and diphenhydramine hydrochloride in the other layer is illustrated as follows:

| Ingredients | Weight/tablet (mgs) | Weight/1 kg batch (gms) |
| --- | --- | --- |
| Layer 1 (Immediate release) | | |
| Diphenhydramine Hydrochloride | 100.0 | 100.0 |
| Silicified Microcrystalline Cellulose | 111.0 | 111.0 |

-continued

| Ingredients | Weight/tablet (mgs) | Weight/1 kg batch (gms) |
|---|---|---|
| Povidone | 3.0 | 3.0 |
| Croscarmellose Sodium | 10.0 | 10.0 |
| Magnesium Stearate | 1.0 | 1.0 |
| Layer 2 (Sustained release) | | |
| Pseudoephedrine HCl | 120.0 | 120.0 |
| Diphenhydramine Hydrochloride | 100.0 | 100.0 |
| Microcrystalline Cellulose (PH 102) | 105.0 | 105.0 |
| Lactose Monohydrate | 100.00 | 100.00 |
| Dicalcium Phosphate | 100.0 | 100.0 |
| Povidone | 15.0 | 15.0 |
| Methocel K4M Premium | 10.0 | 210.0 |
| Stearic Acid | 20.0 | 20.0 |
| Magnesium Stearate | 5.0 | 5.0 |
| Total | 800.0 | 800.0 |

Manufacturing Process (a) Immediate release layer: Screen all ingredients through a USP sieve size #30. Blend diphenhydramine hydrochloride, silicified microcrystalline cellulose and croscarmellose sodium in a high shear mixer/granulator for 10 minutes. Granulate the above blend using a 30% povidone solution (4.3 gms povidone in 14.3 gms purified water). Dry the granulation until the loss on drying (LOD) is less than 2.0%. Screen the dried granulation through a USP sieve size #14. Add the screened granulation and the prescreened magnesium stearate to the above blend and mix for 3 minutes.

(b) Sustained release layer: Screen all ingredients through a USP sieve size #30. Blend the pseudoephedrine hydrochloride, diphenhydramine hydrochloride, Prosolv® (silicified microcrystalline cellulose), lactose monohydrate, dicalcium phosphate, Methocel K4M Premium and stearic acid in a high shear mixer/granulator for 10 minutes. Granulate the above blend using a 30% povidone solution. Dry the granulation until the LOD is less than 2.0%. Screen granules through a USP sieve size #14. Add granules and the prescreened magnesium stearate to the above blend and mix for 3 minutes.

Manufacture bi-layered tablets using a rotary bi-layer tablet press where in each tablet the immediate release layer is 225 mgs and the sustained release layer is 575 mgs.

By using the process described above, a bi-layered tablet of the following composition may be manufactured through wet granulation:

| Ingredients | Weight/tablet (mgs) |
|---|---|
| Layer 1 (Immediate Release) | |
| Diphenhydramine Hydrochloride | 100 |
| Silicified Microcrystalline cellulose | 129.5 |
| Povidone | 4 |
| Croscarmellose sodium | 15 |
| Magnesium Stearate | 1.5 |
| Layer 2 (Sustained Release) | |
| Pseudoephedrine HCl | 120 |
| Diphenhydramine Hydrochloride | 100 |
| Microcrystalline Cellulose 102 | 30 |
| Lactose Monohydrate | 100 |
| Dicalcium Phosphate | 100 |
| Povidone | 15 |
| Hydroxypropylmethylcellulose | 210 |

-continued

| Ingredients | Weight/tablet (mgs) |
|---|---|
| Stearic Acid | 20 |
| Magnesium Stearate | 5 |
| Total | 950 |

The above examples illustrate how to manufacture a bi-layered tablet containing diphenhydramine hydrochloride in one layer and a decongestant and/or an antitussive and/or an expectorant and/or an analgesic in the other layer (optionally in combination with diphenhydramine hydrochloride). One or more of the non-limiting examples of active ingredients which may be used in combination with diphenhydramine hydrochloride depending on the specific therapeutic effect desired are listed in the following Table 1 together with exemplary ranges thereof.

TABLE 1

| Active ingredient | Amount per Tablet | Preferred Amount per Tablet | OTC Daily Dosage |
|---|---|---|---|
| ANTITUSSIVES | | | |
| Chlorphedianol hydrochloride | 0.1-800 mg | 1-250 mg | 100 mg |
| Codeine | 0.1-240 mg | 1-80 mg | 120 mg |
| Codeine phosphate | 0.1-240 mg | 1-80 mg | 120 mg |
| Codeine sulfate | 0.1-480 mg | 1-160 mg | 120 mg |
| Dextromethorphan | 0.1-480 mg | 1-160 mg | 120 mg |
| Dextromethorphan hydrobromide | 0.1-240 mg | 1-80 mg | 120 mg |
| Dextromethorphan polistirex | 0.1-240 mg | 1-80 mg | 120 mg |
| Diphenhydramine citrate | 0.1-1000 mg | 1-300 mg | 228 mg |
| Diphenhydramine hydrochloride | 0.1-400 mg | 1-200 mg | 150 mg |
| Benzonatate | 0.1-800 mg | 100-200 mg | |
| Hydrocodone bitatrate | 0.1-40 mg | 1-20 mg | |
| Dihydrocodeine | 0.1-128 mg | 1-50 mg | |
| Caramiphen edisylate | 0.1-160 mg | 1-60 mg | |
| Carbetapentane tannate | 0.1-480 mg | 1-200 mg | |
| Carbetapentane citrate | 0.1-160 mg | 1-80 mg | |
| Hydromorphone | 0.1-8 mg | 0.1-4 mg | |
| Noscapine | 0.1-200 mg | 1-100 mg | |
| EXPECTORANT | | | |
| Guaifenesin | 0.1-4000 mg | 50-1600 mg | 2400 mg |

Example 5

Extended Release Suspension

| Ingredients | Amount/5 ml |
|---|---|
| Diphenhydramine hydrochloride ion-exchange complex | Equivalent to 12.5 mg Diphenhydramine hydrochloride |
| Phenylepherine ion-exchange complex | Equivalent to 10 mg Phenylepherine HCl |
| Eudragit® L 100 | 0.2 to 2.8 grams |
| Glycerin | 315 mg |
| Polysorbate 80 | 1.5 mg |
| Carbomer (e.g., Carbopol® 974) | 15 mg |
| Methyl Paraben | 9 mg |

-continued

| Ingredients | Amount/5 ml |
|---|---|
| Propyl Paraben | 1 mg |
| Artificial grape flavor | 5 mg |
| FD&C red # 40 dye | 0.5 mg |
| Water | q.s. to 5 mL |

The formula described above serves as a non-limiting example. Any active drug which is in the form of a salt, such as diphenhydramine hydrochloride, codeine phosphate, pseudoephedrine hydrochloride, morphine sulfate, or meperidine hydrochloride can be incorporated as an ion-exchange resin complex.

Procedure (1) Add the appropriate amount of sodium polystyrene sulphonate USP (e.g. Amberlite® IRP 88N) to a diphenhydramine hydrochloride and phenylepherine HCl solution.

(2) Stir the mix for 12 hrs to allow complete drug/resin complex formation.

(3) Separate and dry the insoluble drug/resin complex.

(4) Granulate the drug/resin complex with a delayed release/enteric polymer (e.g. Eugragit® L 100, Kollidon® MAE, Aquacoat® PD) and dry the granules.

(5) Mill the granules, if needed.

(6) To an appropriate amount of water add the following ingredients and dissolve: Carbomer (e.g., Carbopol® 974), glycerin, polysorbate 80, methyl paraben, propyl paraben, artificial grape flavor, FD&C red #40 dye.

(7) Add milled granules.

(8) Add water to make up to a final volume.

(9) Adjust pH to the desired viscosity to keep all the solid materials in suspension.

(10) Agitate at suitable rate to avoid settling of the suspension and maintain a homogeneous product mixture.

(11) Fill in suitable containers ensuring that the product is homogeneous throughout the filling operation.

Example 6

Bi-Layered Tablet (Wet Granulation)

A bilayered tablet in accordance with the present invention which comprises diphenhydramine hydrochloride and guaifenesin in both layers as sustained release layers is illustrated as follows.

Procedure

1. Set aside 0.5 kg of purified water to be used as a rinse in step 4.
2. Prepare a solution using the scale up amounts of Povidone K-30, and the remaining Purified Water.
3. Blend the pre-blend scale up amounts of Guaifenesin USP, Diphenhydramine HCl USP, and Calcium Phosphate Dibasic Anhydrous using a high shear mixer/granulator for 10 minutes.
4. With the mixer/granulator on, pump the solution prepared in step 2 in to the mixer/granulator. After completion, stop the mixer/granulator and rinse the container with the 0.5 kg of purified water set aside in step 1. Pump the rinse water to the mixer/granulator with mixer on. Turn off mixer when completed.
5. Charge the pre-blend scale up amount of Methocel K4M premium to the mixer/granulator and mix for 1 minute.
6. Dry the granulation until the LOD is 1% or less.
7. Pass the dried granulation through a Fitzpatrick Fitzmill fitted with a 109 screen.
8. Screen the final blend raw materials through a 12 mesh screen.
9. Blend the milled granulation from step 7 and the screened materials from step 8 using a V-blender for 20 minutes.
10. Screen the lube blend material through a 30 mesh screen.
11. Charge the screened material from step 10 to the V-blender and blend for 2 minutes.
12. Discharge half of the blended product into properly labeled drums double lined with polyethylene bags and set aside for step 16.
13. Screen the color blend material through a 30 mesh screen.
14. Charge the screened color blend material to the V-blender and blend for 1 minute.
15. Discharge into properly labeled drums double lined with polyethylene bags and set aside for step 16.
16. Compress bi-layered tablets using a rotary bi-layer tablet press where in each tablet layer 1 is 450 mg and layer 2 is 475 mg.

Formula

| | | Amounts | |
|---|---|---|---|
| Process Steps | Ingredients | Dose(mg) | Scale-Up |
| Wet Mix | PURIFIED WATER | 55.000 | 13.750 kg |
| Wet Mix | POVIDONE K-30 USP | 15.000 | 3.750 kg |
| Pre-blend | GUAIFENESIN USP | 600.000 | 150.000 kg |
| Pre-blend | DIPHENHYDRAMINE HCL USP | 100.000 | 25.000 kg |
| Pre-blend | CAL PHOSPHATE DIBASIC ANHYD | 40.000 | 10.000 kg |
| Pre-blend | METHOCEL K4M PREMIUM USP | 16.000 | 4.000 kg |
| Final blend | STEARIC ACID NF | 4.500 | 1.130 kg |
| Final blend | METHOCEL K4M PREMIUM USP | 89.700 | 22.430 kg |
| Lube blend | MAGNESIUM STEARATE NF | 4.500 | 1.130 kg |
| Color blend | FD&C BLUE #1 ALM LAKE | 0.300 | 0.075 kg |
| | Total (wt) | 925.000 g | 231.3 kg |
| | Total (tablets) | 1 | 250,000 |

Example 7

Bi-Layered Tablet (Wet Granulation)

A bilayered tablet in accordance with the present invention which comprises diphenhydramine hydrochloride in a sustained release layer and carbetapentane in an immediate release layer is illustrated as follows.

| Process Steps | Ingredients | Dose(mg) | Scale-Up |
|---|---|---:|---:|
| | Sustained Release Layer | | |
| Wet Mix | PURIFIED WATER | 48.000 | 15.000 kg |
| Wet Mix | POVIDONE K-30 USP | 12.000 | 3.750 kg |
| Pre-blend | DIPHENHYDRAMINE HCl USP | 50.000 | 15.630 kg |
| Pre-blend | CAL PHOSPHATE DIBASIC DIHYD | 15.000 | 4.690 kg |
| Pre-blend | PROSOLV ® SMCC 90 | 125.000 | 39.063 kg |
| Pre-blend | METHOCEL K4M PREMIUM USP | 50.000 | 15.625 kg |
| Final blend | METHOCEL K4M PREMIUM USP | 144.000 | 45.000 kg |
| Lube blend | MAGNESIUM STEARATE NF | 4.000 | 1.250 kg |
| | Layer Weight: | 400.000 | |
| | Immediate Release Layer | | |
| Wet Mix | PURIFIED WATER | 24.000 | 7.500 kg |
| Wet Mix | POVIDONE K-30 USP | 6.000 | 1.875 kg |
| Pre-blend | CARBETAPENTANE CITRATE | 40.000 | 12.500 kg |
| Pre-blend | PROSOLV SMCC 90 | 100.000 | 31.250 kg |
| Pre-blend | LACTOSE MONOHYDRATE #316 | 40.000 | 12.500 kg |
| Pre-blend | SODIUM STARCH GLYCOLATE | 8.000 | 2.500 kg |
| Pre-blend | FD&C BLUE #1 ALUMINUM LAKE | 0.156 | 0.048 kg |
| Final blend | PROSOLV SMCC 90 | 145.688 | 45.528 kg |
| Final blend | LACTOSE MONOHYDRATE #316 | 40.000 | 12.500 kg |
| Final blend | SODIUM STARCH GLYCOLATE | 16.000 | 5.000 kg |
| Final blend | FD&C BLUE #1 ALUMINUM LAKE | 0.156 | 0.048 kg |
| Lube blend | MAGNESIUM STEARATE NF | 4.000 | 1.250 kg |
| | Layer Weight: | 400.000 | |
| | Totals(wt) | 800.000 | 250.000 kg |
| | Totals (tablets) | 1 | 312,500 |

Procedure

Sustained Release Layer (Layer 1)

1. Set aside 0.5 kg of purified water to be used in step 4.
2. Prepare a solution using the scale up amounts of Povidone K-30, and the remaining Purified Water from step 1.
3. Blend the pre-blend scale up amounts of Diphenhydramine HCl USP, Calcium Phosphate Dibasic Dihydrate, and Prosolv SMCC 90 with a high shear mixer/granulator for 10 minutes.
4. With the mixer/granulator on, pump the solution prepared in step 2 in to the mixer/granulator. After completion, stop the mixer/granulator and rinse the container with the purified water set aside in step 1. Pump the rinse water to the mixer/granulator with mixer on. Turn off mixer when completed.
5. Charge the pre-blend scale up amount of Methocel K4M premium to the mixer/granulator and mix for 1 minute.
6. Dry the granulation until the LOD is 4% or less.
7. Pass the dried granulation through a Fitzpatrick Fitzmill fitted with a 14 mesh screen.
8. Screen the final blend scale up amount of Methocel K4M premium through a 14 mesh screen.
9. Blend the milled granulation from step 7 and the screened materials from step 8 using a V-blender for 20 minutes.
10. Screen the lube scale up amount of Magnesium Stearate using a 30 mesh screen.
11. Transfer the screened Magnesium Stearate to the V-blender and blend for 3 minutes. When completed discharge into properly identified drums double lined with polyethylene bags.

Immediate Release Layer (Layer 2)

1. Set aside 0.5 kg of purified water to be used in step 4.
2. Prepare a solution using the scale up amount of Povidone K-30, and the remaining purified water from step 1.
3. Blend the pre-blend scale up amounts of Carbetapentane Citrate, Prosolv SMCC 90, Lactose Monohydrate #316, Sodium Starch Glycolate, and FD&C Blue #1 Aluminum Lake using a high shear mixer/granulator for 10 minutes.
4. With the mixer/granulator on, pump the solution prepared in step 2 in to the mixer/granulator. After completion, stop the mixer/granulator and rinse the container with the purified water set aside in step 1. Pump the rinse water to the mixer/granulator with mixer on. Allow mixture to mix for an additional minute then turn mixer/granulator off.
5. Dry the granulation until the LOD is 4% or less.

6. Pass the dried granulation through a Fitzpatrick Fitzmill fitted with a 14 mesh screen.
7. Screen the final blend scale up amounts of Prosolv SMCC 90, Lactose Monohydrate #316, Sodium Starch Glycolate, and FD&C Blue #1 Aluminum Lake through a 14 mesh screen.
8. Blend the milled granulation from step 6 and the screened materials from step 7 using a V-blender for 20 minutes.
9. Screen the lube scale up amount of Magnesium Stearate using a 30 mesh screen.
10. Transfer the screened Magnesium Stearate to the V-blender and blend for 3 minutes. When completed discharge into properly identified drums double lined with polyethylene bags.
11. Compress bi-layered tablets using a rotary bi-layer tablet press where in each tablet layer 1 is 400.0 mg and layer 2 is 400 mg.

Example 8

Bi-Layered Tablet (Wet Granulation)

A bilayered tablet in accordance with the present invention which comprises diphenhydramine hydrochloride in a sustained release layer and diphenhydramine hydrochloride in an immediate release layer is illustrated as follows.

| Process Steps | Ingredients | Dose(mg) | Scale-Up |
|---|---|---|---|
| Sustained Release Layer | | | |
| Dry Mix | DIPHENHYDRAMINE HCl USP | 100.000 | 13.33 kg |
| Dry Mix | CAL PHOSPHATE DIBASIC DIHYDRATE USP | 64.000 | 8.53 kg |
| Dry Mix | PROSOLV ® SMCC 90 | 45.000 | 6.00 kg |
| Granulating Agent 1 | PURIFIED WATER | 45.000 | 6.00 kg |
| Wet Mix | POVIDONE K-30 USP | 12.000 | 1.60 kg |
| Granulating Agent Rinse | PURIFIED WATER | 5.000 | 0.67 kg |
| Post | METHOCEL K4M PREMIUM USP | 50.000 | 6.67 kg |
| Final blend | METHOCEL K4M PREMIUM USP | 175.000 | 23.33 kg |
| Lube blend | MAGNESIUM STEARATE NF | 4.000 | 0.53 kg |
| | Totals | 450.000 | 60.00 kg |
| Immediate Release Layer | | | |
| Dry Mix | DIPHENHYDRAMINE HCl USP | 100.000 | 13.33 kg |
| Dry Mix | SODIUM STARCH GLYCOLATE | 6.000 | 0.80 kg |
| Dry Mix | FD&C BLUE #1 ALUMINUM LAKE | 0.400 | 0.05 kg |
| Dry Mix | LACTOSE MONOHYDRATE #316 | 20.000 | 2.67 kg |
| Dry Mix | PROSOLV SMCC 90 | 100.000 | 13.33 kg |
| Granulating Agent 1 | PURIFIED WATER | 25.000 | 3.33 kg |
| Wet Mix | POVIDONE K-30 USP | 6.000 | 0.08 kg |
| Granulating Agent Rinse | PURIFIED WATER | 5.000 | 0.67 kg |
| Final blend | PROSOLV SMCC 90 | 30.000 | 4.00 kg |
| Final blend | LACTOSE MONOHYDRATE #316 | 22.200 | 2.96 kg |
| Final blend | SODIUM STARCH GLYCOLATE | 12.000 | 1.60 kg |
| Final blend | FD&C BLUE #1 ALUMINUM LAKE | 0.400 | 0.05 kg |
| Lube blend | MAGNESIUM STEARATE NF | 3.000 | 0.40 kg |
| | Totals | 300.000 | 40.00 kg |

Procedure

Sustained Release Layer (Layer 1)
1. Prepare a solution using Povidone K-30 and purified water.
2. Blend the dry mix scale up amounts of Diphenhydramine HCl, Calcium Phosphate Dibasic Dihydrate, and Prosolv SMCC 90 with a high shear mixer/granulator for 10 minutes.
3. With the mixer/granulator on, pump the solution prepared in step 1 in to the mixer/granulator. After completion, stop the mixer/granulator and rinse the container with purified water. Pump the rinse water to the mixer/granulator with mixer on. Turn off mixer when completed.
4. Charge the post mix scale up amount of Methocel K4M premium to the mixer/granulator and mix for 1 minute.
5. Dry the granulation until the LOD is 4% or less.
6. Resize the dried granulation through a number 14 mesh screen.
7. Screen the final blend scale up amount of Methocel K4M premium through a number 14 mesh screen.
8. Blend the screened materials from step 6 and 7 using a V-blender for 20 minutes.
9. Screen the lube scale up amount of Magnesium Stearate using a number 30 mesh screen.
10. Transfer the screened Magnesium Stearate to the V-blender and blend for 3 minutes. When completed discharge and set aside for step 11.
11. Manufacture bi-layered tablets using a rotary bi-layer tablet press where in each tablet layer 1 is 450.0 mg and layer 2 is 300.0 mg.

Immediate Release Layer (Layer 2)
1. Prepare a solution using the scale up amounts of Povidone K-30, and purified water.
2. Blend the dry mix scale up amounts of Diphenhydramine HCl, Sodium Starch Glycolate, FD&C Blue #1 Aluminum Lake, Lactose Monohydrate #316, and Prosolv SMCC 90 with a high shear mixer/granulator for 10 minutes.
3. With the mixer/granulator on, pump the solution prepared in step 1 in to the mixer/granulator. After completion, stop the mixer/granulator and rinse the container with purified water. Pump the rinse water to the mixer/granulator with mixer on. Allow mixture to mix for an additional minute then turn mixer/granulator off.
4. Dry the granulation until the LOD is 4% or less.
5. Resize the dried granulation through a number 14 mesh screen.
6. Screen the final blend scale up amounts of Prosolv SMCC 90, Sodium Starch Glycolate, FD&C Blue #1 Aluminum Lake, and Lactose Monohydrate #316 through a number 14 mesh screen.
7. Blend the screened materials from step 6 and 7 using a V-blender for 20 minutes.
8. Screen the lube scale up amount of Magnesium Stearate using a number 30 mesh screen.
9. Transfer the screened Magnesium Stearate to the V-blender and blend for 3 minutes. When completed discharge and set aside for step 10.
10. Manufacture bi-layered tablets using a rotary bi-layer tablet press where in each tablet layer 1 is 450.0 mg and layer 2 is 300.0 mg.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A pharmaceutical dosage form, wherein the dosage form comprises at least one of diphenhydramine and a pharmaceutically acceptable salt thereof in a first form or layer and at least one of diphenhydramine and a pharmaceutically acceptable salt thereof in a second form or layer, the first form or layer being a controlled release form or layer and the second form or layer being a controlled release form or layer that is different from the first form or layer and releases the at least one of diphenhydramine and a pharmaceutically acceptable salt thereof at least one of over a different period and at a different rate than the first form or layer.

2. The dosage form of claim 1, wherein the second form or layer releases the at least one of diphenhydramine and a pharmaceutically acceptable salt thereof at least over a different period than the first form or layer.

3. The dosage form of claim 1, wherein the second form or layer releases the at least one of diphenhydramine and a pharmaceutically acceptable salt thereof at least at a different rate than the first form or layer.

4. The dosage form of claim 1, wherein at least one of the first and second forms or layers comprises diphenydramine hydrochloride.

5. The dosage form of claim 1, wherein the dosage form comprises a solid dosage form.

6. The dosage form of claim 5, wherein the dosage form is a tablet.

7. The dosage form of claim 5, wherein the dosage form is a bi-layered tablet.

8. The dosage form of claim 1, wherein the dosage form comprises two different controlled release forms or layers both of which comprise at least one of diphenhydramine and a pharmaceutically acceptable salt thereof and wherein at least one of the forms or layers comprises at least one additional drug.

9. The dosage form of claim 8, wherein the at least one additional drug is selected from decongestants, antitussives, expectorants, mucus thinning drugs, and analgesics.

10. The dosage form of claim 8, wherein the at least one additional drug comprises at least one decongestant.

11. The dosage form of claim 10, wherein the at least one decongestant comprises at least one of phenylepherine and a pharmaceutically acceptable salt thereof.

12. The dosage form of claim 10, wherein the at least one decongestant comprises at least one of pseudoephedrine and a pharmaceutically acceptable salt thereof.

13. The dosage form of claim 8, wherein the at least one additional drug comprises at least one antitussive.

14. The dosage form of claim 13, wherein the at least one antitussive comprises at least one drug selected from codeine, dihydrocodeine, hydrocodone, dextromethorphan, carbetapentane, and pharmaceutically acceptable salts thereof.

15. The dosage form of claim 8, wherein the at least one second drug comprises at least one analgesic.

16. The dosage form of claim 15, wherein the at least one analgesic comprises at least one drug selected from acetaminophen, aspirin, ibuprofen, naproxen, morphine, and pharmaceutically acceptable salts thereof.

17. The dosage form of claim 8, wherein the at least one second drug comprises at least one expectorant.

18. The dosage form of claim 16, wherein the at least one expectorant comprises guaifenesin.

19. The dosage form of claim 8, wherein the dosage form provides a plasma concentration within a therapeutic range of the at least one additional drug over a period which is coextensive with at least 70% of a period over which the dosage form provides a plasma concentration within a therapeutic range of diphenhydramine.

20. The dosage form of claim 19, wherein the at least one additional drug is selected from decongestants, antitussives, expectorants, mucus thinning drugs, and analgesics.

21. The dosage form of claim 19, wherein the dosage form comprises diphenhydramine hydrochloride.

22. The dosage form of claim 19, wherein the at least one additional drug comprises at least one antitussive.

23. The dosage form of claim 22, wherein the at least one antitussive comprises at least one drug selected from codeine, dihydrocodeine, hydrocodone, dextromethorphan, carbetapentane, and pharmaceutically acceptable salts thereof.

24. The dosage form of claim 19, wherein the at least one additional drug comprises at least one decongestant.

25. The dosage form of claim 24, wherein the at least one decongestant comprises at least one drug selected from phenylepherine, pseudoephedrine, and pharmaceutically acceptable salts thereof.

26. The dosage form of claim 19, wherein the at least one additional drug comprises at least one analgesic.

27. The dosage form of claim 19, wherein the at least one additional drug comprises at least one expectorant.

28. The dosage form of claim 27, wherein the at least one expectorant comprises guaifenesin.

29. The dosage form of claim 19, wherein a plasma half-life of the at least one additional drug is shorter or longer than a plasma half-life of diphenhydramine by at least 2 hours.

30. The dosage form of claim 19, wherein a plasma half-life of the at least one additional drug is shorter or longer than a plasma half-life of diphenhydramine by at least 4 hours.

31. The dosage form of claim 19, wherein the period of a plasma concentration within the therapeutic range of the at least one additional drug is coextensive with at least 80% of the period of a plasma concentration within the therapeutic range of diphenhydramine.

32. The dosage form of claim 19, wherein the period of a plasma concentration within the therapeutic range of the at least one additional drug is coextensive with at least 90% of the period of a plasma concentration within the therapeutic range of diphenhydramine.

33. The dosage form of claim 19, wherein the dosage form comprises a tablet.

34. The dosage form of claim 33, wherein the tablet is a bi-layered tablet.

35. A bi-layered tablet which comprises a first layer and a second layer, the first layer being a controlled release layer which comprises at least one of diphenhydramine and a pharmaceutically acceptable salt thereof and the second layer being a controlled release layer which comprises at least one of diphenhydramine and a pharmaceutically acceptable salt thereof and releases the at least one of diphenhydramine and a pharmaceutically acceptable salt thereof at least one of over a different period and at a different rate than the first layer.

36. The bi-layered tablet of claim 35, wherein the second layer releases the at least one of diphenhydramine and a pharmaceutically acceptable salt thereof at least over a different period than the first layer.

37. The bi-layered tablet of claim 35, wherein the second layer releases the at least one of diphenhydramine and a pharmaceutically acceptable salt thereof at least at a different rate than the first layer.

38. The bi-layered tablet of claim 35, wherein at least one of the first and second layers comprises diphenydramine hydrochloride.

39. The bi-layered tablet of claim 35, wherein at least one of the first and second layers comprises at least one additional drug.

40. The bi-layered tablet of claim 39, wherein the at least one additional drug is selected from decongestants, antitussives, expectorants, mucus thinning drugs, and analgesics.

41. The bi-layered tablet of claim 39, wherein the at least one additional drug comprises at least one decongestant.

42. The bi-layered tablet of claim 41, wherein the at least one decongestant comprises at least one of phenylepherine and a pharmaceutically acceptable salt thereof.

43. The bi-layered tablet of claim 41, wherein the at least one decongestant comprises at least one of pseudoephedrine and a pharmaceutically acceptable salt thereof.

44. The bi-layered tablet of claim 39, wherein the at least one additional drug comprises at least one antitussive.

45. The bi-layered tablet of claim 44, wherein the at least one antitussive comprises at least one drug selected from codeine, dihydrocodeine, hydrocodone, dextromethorphan, carbetapentane, and pharmaceutically acceptable salts thereof.

46. The bi-layered tablet of claim 39, wherein the at least one second drug comprises at least one analgesic.

47. The bi-layered tablet of claim 46, wherein the at least one analgesic comprises at least one drug selected from acetaminophen, aspirin, ibuprofen, naproxen, morphine, and pharmaceutically acceptable salts thereof.

48. The bi-layered tablet of claim 39, wherein the at least one second drug comprises at least one expectorant.

49. The bi-layered tablet of claim 48, wherein the at least one expectorant comprises guaifenesin.

50. The bi-layered tablet of claim 39, wherein the bi-layered tablet provides a plasma concentration within a therapeutic range of the at least one additional drug over a period which is coextensive with at least 70% of a period over which the bi-layered tablet provides a plasma concentration within a therapeutic range of diphenhydramine.

51. The bi-layered tablet of claim 50, wherein the at least one additional drug is selected from decongestants, antitussives, expectorants, mucus thinning drugs, and analgesics.

52. The bi-layered tablet of claim 50, wherein the dosage form comprises diphenhydramine hydrochloride.

53. The bi-layered tablet of claim 50, wherein the at least one additional drug comprises at least one antitussive.

54. The bi-layered tablet of claim 53, wherein the at least one antitussive comprises at least one drug selected from codeine, dihydrocodeine, hydrocodone, dextromethorphan, carbetapentane, and pharmaceutically acceptable salts thereof.

55. The bi-layered tablet of claim 50, wherein the at least one additional drug comprises at least one decongestant.

56. The bi-layered tablet of claim 55, wherein the at least one decongestant comprises at least one drug selected from phenylepherine, pseudoephedrine, and pharmaceutically acceptable salts thereof.

57. The bi-layered tablet of claim 50, wherein the at least one additional drug comprises at least one analgesic.

58. The bi-layered tablet of claim 50, wherein the at least one additional drug comprises at least one expectorant.

59. The bi-layered tablet of claim 58, wherein the at least one expectorant comprises guaifenesin.

60. The bi-layered tablet of claim 50, wherein a plasma half-life of the at least one additional drug is shorter or longer than a plasma half-life of diphenhydramine by at least 2 hours.

61. The bi-layered tablet of claim 50, wherein a plasma half-life of the at least one additional drug is shorter or longer than a plasma half-life of diphenhydramine by at least 4 hours.

62. The bi-layered tablet of claim 50, wherein the period of a plasma concentration within the therapeutic range of the at least one additional drug is coextensive with at least 80% of the period of a plasma concentration within the therapeutic range of diphenhydramine.

63. The bi-layered tablet of claim 50, wherein the period of a plasma concentration within the therapeutic range of the at least one additional drug is coextensive with at least 90% of the period of a plasma concentration within the therapeutic range of diphenhydramine.

64. The bi-layered tablet of claim 35, wherein the first layer comprises only diphenhydramine or a pharmaceutically acceptable salt thereof as an active ingredient.

65. The bi-layered tablet of claim 50, wherein the first layer comprises only diphenhydramine hydrochloride as an active ingredient.

66. The bi-layered tablet of claim 35, wherein the first layer comprises from about 10 mg to about 300 mg of diphenhydramine hydrochloride or an equivalent amount of at least one other pharmaceutically acceptable salt of diphenhydramine.

67. The bi-layered tablet of claim 66, wherein the second layer comprises from about 2.5 mg to about 300 mg of diphenhydramine hydrochloride or an equivalent amount of at least one other pharmaceutically acceptable salt of diphenhydramine.

68. The bi-layered tablet of claim 67, wherein the second layer comprises one or more of (i) from about 1 mg to about 120 mg of phenylepherine hydrochloride or an equivalent amount of at least one other pharmaceutically acceptable salt of phenylepherine; (ii) from about 1 mg to about 240 mg of pseudoephedrine hydrochloride or an equivalent amount of at least one other pharmaceutically acceptable salt of pseudoephedrine; (iii) from about 1 mg to about 120 mg of carbetapentane citrate or an equivalent amount of at least one other pharmaceutically acceptable salt of carbetapentane; (iv) from about 1 mg to about 120 mg of codeine phosphate or an equivalent amount of at least one other pharmaceutically acceptable salt of codeine; (v) from about 1 mg to about 30 mg of dihydrocodeine bitartrate or an equivalent amount of at least one other pharmaceutically acceptable salt of dihydrocodeine; (vi) from about 1 mg to about 20 mg of hydrocodone bitartrate or an equivalent amount of at least one other pharmaceutically acceptable salt of hydrocodone; (vii) from about 10 mg to about 1000 mg of acetaminophen; and (viii) from about 10 mg to about 1500 mg of guaifenesin.

* * * * *